United States Patent [19]

Narisada et al.

[11] 4,371,532

[45] Feb. 1, 1983

[54] MALONAMIDOOXADETHIACEPHEM COMPOUNDS

[75] Inventors: Masayuki Narisada, Ibaraki; Tetsuo Okada, Sakai, both of Japan

[73] Assignee: Shionogi & Co., Ltd., Osaka, Japan

[21] Appl. No.: 227,202

[22] Filed: Jan. 22, 1981

[30] Foreign Application Priority Data

Jan. 22, 1980 [JP] Japan .................................. 55-5313

[51] Int. Cl.³ .................. C07D 413/14; C07D 498/04; A61K 31/535; A61K 31/425
[52] U.S. Cl. ................................. 424/248.51; 544/90; 424/248.52
[58] Field of Search ...................... 544/90; 424/248.51, 424/248.52

[56] References Cited

U.S. PATENT DOCUMENTS

| | | | |
|---|---|---|---|
| 4,138,486 | 2/1979 | Narisada et al. | 544/90 |
| 4,180,571 | 12/1979 | Narisada et al. | 544/90 |
| 4,226,866 | 10/1980 | Christensen et al. | 544/90 |
| 4,232,151 | 11/1980 | Nagata et al. | 544/90 |
| 4,259,485 | 3/1981 | Wheeler | 544/90 |
| 4,323,567 | 4/1982 | Narisada et al. | 544/90 |

FOREIGN PATENT DOCUMENTS 53-84987 7/1978 Japan ..................................... 544/90
53-149991 12/1978 Japan ..................................... 544/90

*Primary Examiner*—John M. Ford
*Attorney, Agent, or Firm*—Wenderoth, Lind & Ponack

[57] ABSTRACT

An antibacterial compound represented by the following formula:

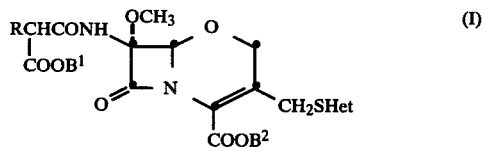

(wherein
R is a hydrogen atom or a lower alkyl, lower alkenyl, lower alkynyl or lower alkylthio-lower alkyl group;
$B^1$ and $B^2$ each is a hydrogen atom or an ester or salt forming group or atom same or different for each; and
Het is a monocyclic hetero-cyclic group)

showing strong antipseudomonal activity, process for preparing the same, pharmaceutical preparation containing the same and method for combating bacterial infection by applying the same.

15 Claims, No Drawings

MALONAMIDOOXADETHIACEPHEM COMPOUNDS

This invention relates to novel 7β-(substituted malonamido or unsubstituted malonamido)-7α-methoxy-3-heterocyclic thiomethyl-1-oxa-1-dethia-3-cephem-4-carboxylic acid compounds, methods for preparing them, antibacterial use and preparations utilizing the said compounds.

I. COMPOUNDS

More specifically, this invention relates to a compound represented by the following formula:

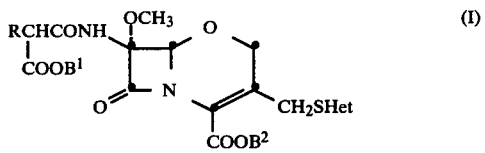

(wherein
R is a hydrogen atom or a lower alkyl, lower alkenyl, lower alkynyl or lower alkylthio-lower alkyl group;
$B^1$ and $B^2$ each is a hydrogen atom or an ester or salt forming group or atom; same or different for each; and
Het is a monocyclic heterocyclic group).

Characteristics

The malonamidooxadethiacephem compounds (I) have strong antibacterial activity. They are superior to their analogs (Japanese Published Patent Application No. 133,997/1977) having an aromatic group in place of the R group of the formula (I) in the effect for protecting mice from infections caused by gram-negative bacteria e.g. Pseudomonas aeruginosa, height of blood level, chemical stability and easiness to purify. Thus, the compounds are useful as β-lactam antibacterials for medicines, veterinary drugs, sterilizers, disinfection agents, sanitizing substances and so forth.

Explanation of Symbols

Preferable substituents R as a lower alkyl, lower alkenyl or lower alkynyl group for the malonamido substituent in the formula (I) include $C_1$ to $C_6$ (especially $C_1$ or $C_2$)-alkyl, $C_2$ to $C_5$-alkenyl and $C_2$ to $C_5$-alkynyl. Preferable lower alkylthio-lower alkyl group are $C_1$ to $C_2$-alkylthio-$C_1$ to $C_2$-alkyl.

Preferable monocyclic heterocyclic groups Het are 5 or 6-membered ring groups having 1 to 4-hetero atoms (O, N and/or S) optionally substituted e.g. by $C_1$ to $C_5$-alkyl, carboxyalkyl, aminoalkyl, halogen, hydroxy and/or oxo.

$B^1$ and $B^2$ each is a hydrogen atom or a carboxy modification conventional in the chemistry of penicillins and cephalosporins. Preferable ester group as a protecting group during a chemical treatment can be e.g. mono- or dicyclic aralkyl, $C_4$ to $C_{10}$-tertiary alkyl, $C_1$ to $C_{10}$-β-haloalkyl or $C_3$ to $C_8$-β-alkylsulfonylalkyl; and as a pharmacologically acceptable ester can be straight or branched chain $C_3$ to $C_{19}$-alkanoyloxyalkyl, $C_3$ to $C_6$-alkoxycarbonyloxyalkyl, $C_4$ to $C_6$-tertiary alkyl, $C_7$ to $C_9$-aralkyl or aryl esters. Preferable salt forming atom can be a light metal atom e.g. alkali metal or alkaline earth metal atom, especially sodium atom. Preferable salt forming group can be ammonium, $C_1$ to $C_{10}$-primary to quaternary ammonium group or alkanoyloxy-alkaline earth metal group.

More specifically preferable compounds include those having $C_1$ to $C_3$-alkyl as R; five-membered heterocyclic group having three to four hetero atoms selected from oxygen, nitrogen and sulfur and optionally substituted by $C_1$ to $C_2$-alkyl as Het; and hydrogens as $B^1$ and $B^2$. Sodium, potassium and calcium salts, and $C_2$ to $C_5$-alkanoyloxy-$C_1$ to $C_3$-alkyl esters thereof are also another group of more preferable compounds.

Most preferable R is methyl or ethyl; Het is 1,3,4-thiadiazol-2-yl, 2-methyl-1,3,4-thiadiazol-5-yl or 1-methyltetrazol-5-yl; and $B^1$ and $B^2$ are hydrogens. The most preferable compounds can be in sodium salt or $C_2$ to $C_5$-alkanoyloxy-$C_1$ or $C_2$-alkyl ester forms thereof.

II. SYNTHESIS

The compounds of the formula (I) can be prepared by the following reactions:

(1) Acylation

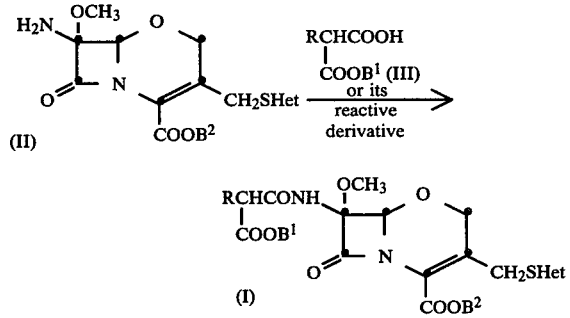

(wherein, R, Het, $B^1$ and $B^2$ are as defined above).

By this acylation, Malonic acid (III) or its reactive derivative is reacted with Methoxyamine compound (II) known from e.g. Japanese Published Patent Application No. 133,594/1974. Malonic acid compound (III) is used in the presence of a dehydrating condensing reagent e.g. dicyclohexylcarbodiimide or 1-ethoxycarbonyl-2-ethoxy-1,2-dihydroquinoline. The reactive derivative of the Malonic acid compound (III) can be used in the presence of a reaction-promoting reagent e.g. a base. These are conventional methods well-known in the art of chemistry of β-lactam antibacterials. Especially preferable reactive derivatives are acid halogenides, acid anhydrides, and reactive esters. Preferable reaction-promoting reagents are aromatic bases and tertiary amines. The acylation is usually carried out at −20° C. to 60° C. in a conventional inert solvent. The product can be isolated by a conventional method.

(2) Deprotection of Carboxy-Protecting Group

When $B^1$ or $B^2$ is a carboxy-protecting group, this is deprotected to produce the corresponding carboxy compound (I) where said $B^1$ or $B^2$ is hydrogen. The method can be that specific to the protective group. Preferably, the method can also be that conventional in the chemistry of β-lactam antibacterials. Representatives are the hydrolysis of tertiary alkyl ester with a mineral acid; fission of an aralkyl ester with strong carboxylic acid or Lewis acid in the presence of anisole; hydrolysis with aqueous base; and the reduction of p-nitrobenzyl ester or haloalkyl ester; each operated under conventional conditions e.g. at −20° C. to 60° C. in an inert solvent, to isolate the product by usual method with good results.

(3) Formation of Salt

By the action of a base or exchange decomposition reaction of Compound (I) where $B^1$ or $B^2$ is hydrogen, the corresponding salt can be prepared. This may be done in an inert solvent at −20° C. to 60° C. If the solvent is suitably less polar, the objective salt usually precipitates. If required, a neutral salt solution may be lyophilized to obtain the product as powder.

(4) Esterification

By reacting a reactive derivative of alcohol with a salt of Compound (I) where $B^1$ or $B^2$ is hydrogen, or by reacting alcohol with activated carboxylic acid of Compound (I) in the form of e.g. acid halide, acid anhydride or reactive ester, the corresponding esteric Compound (I) can be prepared. The reaction can usually be carried out in an inert solvent at −20° C. to 60° C.

(5) Other Methods

In addition to above (1) to (4), Compound (I) can be prepared by the introduction of methoxy or Het-S group, or modification of substituent according to the manner conventional in the chemistry of $\beta$-lactam antibacterials.

These reactions may be done in a manner conventional in the chemistry of $\beta$-lactam antibacterials. If required, one or more of above procedures can be made in one and the same vessel, with or without removal of the reaction solvent used. The intermediates may be isolated or used without such isolation to the next reaction.

III. USAGE

Antibacterial Use

The compounds (I) of this invention show stronger antibacterial activity against sensitive gram-positive and gram-negative bacteria and may be used for preventing or treating bacterial infections in human, veterinary or poultry field. For example, enteral or parenteral administration, especially intravenus or intramuscular or drip administration of the salt compounds prevents or cures bacterial infections caused by a sensitive bacteria in man at a daily dose of e.g. 0.5 to 2 g. In the case of topical administration, the dose can be much smaller.

Synthetic Use

For example, the Compound (I) having a protective group for chemical reactions are useful as intermediates for preparing antibacterial carboxylic acid by deprotection; free acids and its salts are interconvertible and also are useful starting material for each other to show another utility of this invention; and these are also useful for production of esters. As is exemplified above, the compounds are also useful as starting material for synthetic production.

IV. COMPOSITIONS

The compound (I) can be used in a wide variety of oral or parenteral dosage forms solely or in admixture with other coacting substances. The pharmaceutical compositions may be a mixture of 0.01 to 99% of Compound (I) with a pharmaceutical carrier which can be a solid material or liquid material in which the compounds are dissolved, dispersed or suspended. They can be in a unit dosage form. The solid compositions can take the form of tablets, powder, dry syrups, troches, granules, capsules, pills, suppositories or like solid preparations. The liquid compositions can take the forms of injections, ointments, dispersions, inhalant, suspensions, solution, emulsions, syrups or elixirs. They may be flavored, colored and tablets, granules and capsules may be coated.

V. METHOD OF USE

This invention also provides a method for treating or preventing human or veterinary bacterial infections by administering to the human or animal subject an effective amount of Compound (I) at a daily dose of e.g. 0.1 to 50 mg per kilogram body weight for injection or e.g. 1 to 100 mg milligram per kilogram body weight for oral administration, at an interval of e.g. 3 to 12 hours. For topical application, 1 to 100 $\mu$g may be applied.

The method is applicable for treating or preventing diseases caused by a sensitive strain of bacteria e.g. gram-positive *Staphylococcus aureus, Streptococcus pyogenes, Bacillus subtilis, Bacillus cereus, Diplococcus pneumoniae, Corynebacterium diphtheriae* and gram-negative *Escherichia coli, Klebsiella pneumoniae, Enterobacter cloacae, Shigella Sonnei, Salmonella paratyphi, Salmonella typhi, Serratia marsescens* and *Pseudomonas aeruginosa* bacteria.

Representative diseases caused by above bacteria include pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections and pyelonephritis.

VI. PRIOR ART

The prior art most closely related to this invention are U.S. Pat. Nos. 4,138,486, 4,201,782 and 4,226,866 disclosing 1-dethia-1-oxacephalosporins.

Following examples illustrate the embodiment of this invention.

When R is not hydrogen, the α-carbon of 7-malonamido side chain is an asymmetric carbon. D- and L-stereoisomers of Compound (I) can be produced by selecting suitable starting malonic acid (III) in a sterically pure form or separation of an isomeric mixture-product.

Followings are the abbreviations used in Examples. AOM is for acetoxymethyl. MeTdz is for 2-methyl-1,3,4-thiadiazol-5-yl. POM is for pivaloyloxymethyl. Ph is for phenyl. Tetr is for 1-methyl-5-tetrazolyl. Tdz is for 2-thiadiazolyl. ca. shows about.

Physical constants of the products and the structural change caused by the reaction indicated by an arrow mark accompanied with the yield in percent are shown at the suitable positions in the Tables given at the end of each Examples.

Amounts of the starting materials, reagents and solvents are expressed in the allowable ratio to the oxacephem starting material in each examples for obtaining good results.

EXAMPLE 1A

Acylation in Tetrazolyl series (Het=Tetr)

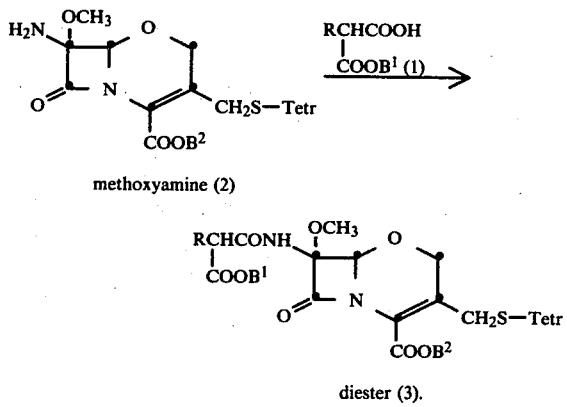

methoxyamine (2)

diester (3).

To a solution of malonic acid half ester (1) (2.2 equivalents) in dichloromethane (9 weights) are added triethylamine (1 to 2 equivalents) and oxalyl chloride or phosphorus oxychloride (1 to 2 equivalents) with stirring at −25° C. under nitrogen atmosphere. The mixture is stirred at −10° to 10° C. for 1 to 3 hours. This is mixed with a suspension of methoxyamine (2) (1 equivalent, 1 weight) and pyridine (1.1 to 3 equivalents) in dichloromethane (10 to 30 weights). The mixture is stirred at −10° to 10° C. for 1 to 3 hours. The reaction mixture is diluted with benzene, washed with 2 N-hydrochloric acid, water, aqueous 5% sodium hydrogen carbonate and water, dried over magnesium sulfate and concentrated to dryness. The residue is chromatographed over silica gel containing 10% water, and the fraction eluted with benzene-ethyl acetate (7:1) mixture is concentrated to obtain diester (3).

By this method, the compounds of Table 1 can be obtained.

TABLE 1

Acylation in Tetrazolyl series (Het = Tetr)

| No. | R | $B^1$ | $B^2$ | yield (%) | shape | IR:$\nu_{max}^{CHCl_3}$ cm$^{-1}$ | NMR: $\delta_{ppm}^{CDCl_3}$ (Hz value = J value) |
|---|---|---|---|---|---|---|---|
| 1 | —H | —CHPh$_2$ | —CHPh$_2$ | 96 | powder | 3320, 1790, 1720. | 3,47s3H, 3.48s2H, 3.75s3H, 4.23s2H, 4.55s2H, 5.00s1H, 6.90s2H. |
| 2 | —CH$_3$ | —CHPh$_2$ | —CHPh$_2$ | 99 | powder | 3300, 1792, 1720. | 1.50d(7Hz)3H, 3.4brs1H, (3.38s + 3.43s)3H, 3.75s3H, 4.23 s2H, 4.50s2H, 5.00s1H, 6.87s2H |
| 3 | —C$_2$H$_5$ | —CHPh$_2$ | —CHPh$_2$ | quant | powder | 3340, 1785, 1718. | 0.87t(7Hz)3H, 1.97dq(8;8Hz)2H, 3.3brs1H, 3.36s3H, 3.73s3H, 4.18s2H, 4.43s2H, 4.95s1H, 6.83s2H. |
| 4 | —n-C$_3$H$_7$ | —CHPh$_2$ | —CHPh$_2$ | 99 | powder | 3310, 1793, 1720.. | 0.6–2.3m7H, 3.40s3H, 3.47t (6Hz)1H, 3.73s3H, (4.22s + 4.25 s)2H, 4.50s2H, 5.00s1H, 6.92 s2H. |
| 5 | —i-C$_3$H$_7$ | —CHPh$_2$ | —CHPh$_2$ | 72 | powder | 3340, 1783, 1720. | 0.92d(7Hz)3H, 1.03d(7Hz)3H, 2.4m1H, 3.16d(8Hz)1H, (3.32s + 3.43s)3H, 3.77s3H, (4.22s + 4.30s)2H, (4.45s + 4.57s)2H, (4.93s + 4.98s)1H, 6.87s2H. |
| 6 | —i-C$_4$H$_9$ | —CHPh$_2$ | —CHPh$_2$ | 97 | powder | 3320, 1787, 1718. | 1.03d(6Hz)6H, 1.83t(7Hz)2H, 1.9m1H, 3.38s3H, 3.50t(7Hz) 1H, 3.70s3H, (4.16s + 4.21s)2H, 4.45s2H, 4.97s1H, 6.88s2H. |
| 7 | —n-C$_6$H$_{13}$ | —CHPh$_2$ | —CHPh$_2$ | 75 | powder | — | 0.6–2.2m13H, 3.37s3H, 3.43t (6Hz)1H, 3.68s3H, 4.18s2H, 4.47s2H, 4.98s1H, 6.90s2H. |
| 8 | —CH$_2$CH=CH$_2$ | —CHPh$_2$ | —CHPh$_2$ | 96 | powder | 3330, 1793, 1720. | 2.70t(7Hz)2H, 3.40s3H, 3.50t (7Hz)1H, 3.73s3H, 4.38s2H, 4.48s2H, 4.97s1H, 4.7–5.2m2H, 5.4–6.2m1H, 6.87s2H. |
| 9 | —CH$_2$C≡CH | —CHPh$_2$ | —CHPh$_2$ | 97 | powder | 3400, 3300, 1787, 1720. | 2.00s1H, 2.85brd(6Hz)2H, (3.37s + 3.43s)3H, 3.63s3H, 3.6brs1H, 4.18s2H, (4.40s + 4.47s)2H, 4.98s1H, 6.90s2H. |
| 10 | —CH$_2$CH$_2$<br>\|<br>SCH$_3$ | —CHPh$_2$ | —CHPh$_2$ | quant | powder | 3400, 1790, 1722. | 1.97s3H, 2.3–2.7m4H, (3.38s + 3.41s)3H, 3.75s3H, 3.7brs1H, 4.23s2H, 4.50s2H, 6.83s2H. |
| 11 | —C$_2$H$_5$ | —t-C$_4$H$_9$ | —CHPh$_2$ | 82 | powder | 3300–3400, | 0.97t(7Hz)3H, 1.48s9H, 1.93 |

TABLE 1-continued

Acylation in Tetrazolyl series (Het = Tetr)

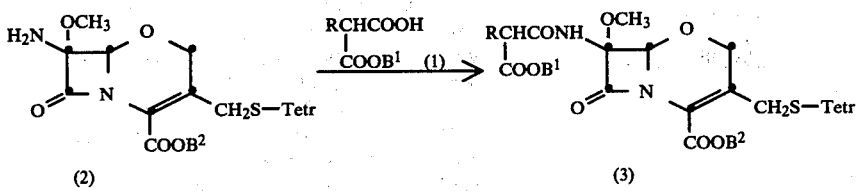

| | | | | diester (3) | | |
|---|---|---|---|---|---|---|
| No. | R | $B^1$ | $B^2$ | yield (%) | shape | IR:$\nu_{max}^{CHCl_3}$cm$^{-1}$ | NMR: $\delta_{ppm}^{CDCl_3}$(Hz value = J value) |
| | | | | | | 1790, 1715. | dq(7;7Hz)2H, 3.13t(7Hz)1H, (3.50s + 3.57s)3H, 3.80s3H, 4.27s2H, 4.60s2H, (5.00s + 5.01s)1H, 6.88s1H. |
| 12 | —CH$_3$ | —Si(CH$_3$)$_3$ —H | —CHPh$_2$ | 73 | powder | 3298, 1785, 1724, 1637 (Nujol). | (1.38d(8Hz) + 1.42d(8Hz))3H, 3.53s3H, 3.65q(8Hz)1H, 3.87s 3H, 4.27s2H, 4.63s2H, (5.07s 5.10s)1H, 6.92s1H, 7.2-7.8m, 8.20m1H(CD$_3$COCD$_3$). |
| 13 | —C$_2$H$_5$ | —Si(CH$_3$)$_3$ —H | —CHPh$_2$ | quant | powder | 3200-3400, 1785, 1720, 1700sh. | 0.97t(7Hz)3H, 1.97dq(7;7Hz) 2H, 3.33t(7Hz)1H, 3.53s3H, 3.75s3H, 4.20s2H, 4.57s2H, 5.03s1H, 6.87s1H. |

Compounds No. 12 and 13: an example of trimethylsilyl ester as $B^1$

To a solution of 2-ethylmalonic acid bis-trimethylsilyl ester (1) (1.8 equivalents) in benzene (10 weights) are added N,N-dimethylformamide (0.1 equivalent) and thionyl chloride (1.5 equivalents) at room temperature. The mixture is stirred for 2.5 hours and concentrated under reduced pressure to give half ester chloride. This is dissolved in dichloromethane (4 weights), and added to a mixture of methoxyamine (2) (1 equivalent, 1 weight), pyridine (1.2 equivalents) and dichloromethane (20 weights) under ice cooling, and the mixture is worked up by the conventional method as given above to afford carboxylic acid Compound No. 12 or 13 (3, $B^1$=H) due to hydrolysis of the trimethylsilyl group.

EXAMPLE 1B

Acylation in Thiadiazolyl series (Het=Tdz)

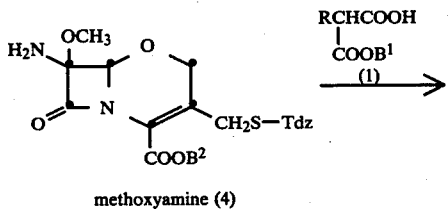

methoxyamine (4)

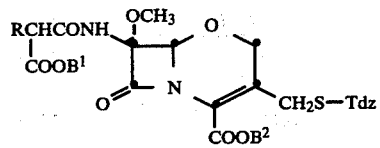

diester (5)

A mixture of methoxyamine (4) (1 equivalent, 1 weight) and pyridine (2 to 3 equivalents) in dichloromethane (10~20 weights) are portionwise mixed under nitrogen with a cooled solution of malonic acid half ester (1) (1 to 1.5 equivalent), pyridine (2 to 3 equivalents) and phosphorus oxychloride (1 to 1.5 equivalents) in dichloromethane prepared at 0° C. for 30 minutes. The resulting mixture is kept at —40° C. with stirring during the addition, and 0° C. for 30 minutes for the reaction under nitrogen. The reaction mixture is diluted with ethyl acetate, washed with 2 N-hydrochloric acid, water, aqueous 5% sodium hydrogen carbonate and water, dried over magnesium sulfate and concentrated to dryness. The residue is chromatographed over silica gel containing 10% water. The fraction eluted with a mixture of benzene and ethyl acetate (5:1) affords diester (5) by concentration.

Compounds of Table 2 are prepared by this method.

TABLE 2

Acylation in Thiadiazolyl series (Het = Tdz)

$$\text{(2)} \xrightarrow{\underset{\text{COOB}^1}{\text{RCHCOOH}} \ (1)} \text{(3)}$$

Structure (2): H₂N–, OCH₃ on β-lactam ring fused with CH₂S—Tdz substituent, COOB² ester.
Structure (3): RCHCONH–, OCH₃ on β-lactam ring fused with CH₂S—Tdz substituent, COOB² ester; side chain has COOB¹.

| No. | R | B¹ | B² | yield (%) | shape | IR:$\nu_{max}^{CHCl_3}$cm$^{-1}$ | NMR: $\delta_{ppm}^{CDCl_3}$ (Hz value = J value) |
|---|---|---|---|---|---|---|---|
| 1 | —CH₃ | —CHPh₂ | —CHPh₂ | 74 | powder | 3350, 1784, 1720. | 1.49d(7Hz)3H, (3.35s + 3.40s)3H, 3.51q(7Hz)1H, 4.2–4.7m4H, 4.99s1H, 6.88s1H, 6.92s1H, 8.87s1H. |
| 2 | —C₂H₅ | —CHPh₂ | —CHPh₂ | 75 | powder | 3350, 1785, 1720. | 0.90t(7Hz)3H, 1.97dq(7;7Hz)2H, 3.40t(7Hz)1H, 3.43s3H, 4.2–4.6m4H, 4.99s1H, 6.90s1H, 6.93s1H, 8.83s1H. |
| 3 | —n-C₃H₇ | —CHPh₂ | —CHPh₂ | 76 | powder | 3400–3300, 1785, 1718. | 0.7–2.1m7H, 3.40s3H, 3.41t(3Hz)1H, (4.33s + 4.46s)2H, 4.50s2H, 5.01s1H, 6.93s1H, 6.94s1H, 8.90s1H. |
| 4 | —n-C₄H₉ | —CHPh₂ | —CHPh₂ | 70 | powder | 3300–3400, 1785, 1718. | 0.6–2.3m9H, 3.40s3H, 3.50t(6Hz)1H, 4.1–4.8m4H, 4.99s1H, 6.83s1H, 8.80s1H. |
| 5 | —CH₂<br>\|<br>CH=CH₂ | —CHPh₂ | —CHPh₂ | 70 | powder | 3345, 1785, 1720. | 2.72t(7Hz)2H, 3.40s3H, 3.4 brs1H, 4.1–4.7m4H, 4.8–5.3m 2H, 4.98s1H, 5.4–6.1m1H, 6.88s1H, 6.93s1H, 8.82s1H. |
| 6 | —C₂H₅ | —Si(CH₃)₃<br>—H | —CHPh₂ | 80 | powder | ca3300, 1785, 1715. | 0.97t(7Hz)3H, 2.03dq(7;7Hz)2H, 3.37t(7Hz)1H, (4.30d + 4.47d)ABq(10Hz)2H, 4.60s2H, 5.08s1H, 6.91s1H, 7.93brs1H, 8.98s1H. |

EXAMPLE 1C

Acylation in Methylthiadiazolyl series (Het=MeTdz)

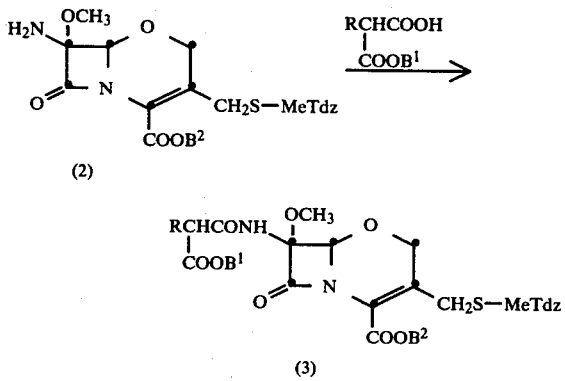

To a solution of methoxyamine (1 weight, 1 equivalent) in dichloromethane (10 to 20 weights) cooled at −22° to −40° C. are added ethylmalonic acid monobenzhydryl ester (1 to 1.5 equivalents) pyridine (4 to 6 equivalents) and phosphorus oxychloride (1 to 2 equivalents). The mixture is stirred at 0° C. for 1 to 2 hours. The reaction mixture is concentrated under reduced pressure. The obtained residue is dissolved in ethyl acetate, washed with diluted hydrochloric acid, water, aqueous diluted sodium hydrogen carbonate and water, dried over magnesium sulfate and evaporated to remove the solvent. The residue is purified by chromatography over silica gel containing 10% water to give objective product (3) from the fraction eluted with benzene and ethyl acetate (7:1) mixture.

R=C₂H₅, B¹=—CHPh₂, B²=—CHPh₂:
IR: $\nu_{max}^{CHCl_3}$ 3400, 1780, 1718.
NMR: $\delta_{ppm}^{CDCl_3}$ 0.92t(7 Hz)3H, 2.00dq(7;7 Hz)2H, 2.67s3H, 3.37t (7 Hz)1H, 3.40s3H, (4.20d(12 Hz)1H+4.50d)ABq(12 Hz)2H, 4.47s2H, 5.00s1H, 6.92s2H, 7.50brs1H.

EXAMPLE 2A

Deesterification in Tetrazolyl series (Het=Tetr)

with CF₃COOH

To an ice-cold solution of ester (3) (1 weight) in dichloromethane (3 to 10 weights) are added anisole (1 to 3 weights) and trifluoroacetic acid (1 to 2 weights). The mixture is stirred for 1 hour, diluted with benzene, and concentrated in vacuo under reduced pressure. The residue is triturated in a mixture of ether and petroleum ether to pulverize the product, filtered to collect it and washed with the same solvent to give dicarboxylic acid or its monoester (6).

with AlCl₃

To a solution of diester (3) (1 weight) in a mixture of dichloromethane (5 to 10 weights) and anisole (3 to 10 weights) is added aluminum chloride (1 to 3 weights) at −20° C. The mixture is stirred at the same temperature for 1 hour. The reaction mixture is diluted with n-hexane to separate precipitate thus formed. This is collected by filtration. The filtrate is extracted with aqueous 5% sodium hydrogen carbonate. The extract is combined with above precipitate and washed with ether. The mixture is acidified with 2 N-hydrochloric acid, saturated with sodium chloride and extracted with methyl ethyl ketone. The extract is dried over magnesium fulfate and concentrated to dryness giving carboxylic acid (7).

Compounds of Table 3 are prepared by this method.

TABLE 3

Deesterification in Tetrazolyl series (Het = Tetr)

| No. | R | $B^1$ | $B^2$ | shape | IR: $\nu_{max}^{KBr}$ cm$^{-1}$ | NMR: $\delta_{ppm}^{CD3COCD3}$ (Hz value = J value) |
|---|---|---|---|---|---|---|
| 1 | —H | —CHPh$_2$ / —H quant | —CHPh$_2$ / —H | powder | 3350br, 1788, 1707. | 3.50s5H, 3.98s3H, 4.32s2H, 4.63s2H, 5.07s1H. |
| 2 | —CH$_2$ | —CHPh$_2$ / —H quant | —CHPh$_2$ / —H | powder | 3292br, 1785, 1720. | (1.32d(7Hz) + 1.36d(7Hz))3H, 3.48 s3H, 3.5brs1H, 3.98s3H, 4.32s2H, 4.63s2H, 5.06s1H. |
| 3 | —CH$_3$ | —AOM | —CHPh$_2$ / —H 99% / —Na | | 3250, 1755, 1765, 1690, 1680, 1640, 1605(Nujol). | 1.38m3H, 2.07s3H, 3.52s2H, 4.00 s3H, 4.50m2H, 4.65brs2H, 5.08s 1H, 5.78s2H. |
| 4 | —CH$_3$ | —POM | —CHPh$_2$ / —H 94% / —Na | powder | 3250, 1760, 1685, 1605. (Nujol) | 1.17s9H, 1.35br3H, 3.48s3H, 3.93 s3H, 4.50m4H, 5.02s1H, 5.75s2H. |
| 5 | —C$_2$H$_5$ | —CHPh$_2$ / —H 85% | —CHPh$_2$ / —H | powder | 3250br, 1780, 1715. | 0.95t(7Hz)3H, 1.90dq(7;7Hz)2H, 3.48s3H, 3.5brs1H, 3.97s3H, 4.31s2H, 4.63s2H, 5.07s1H. |
| 6 | —C$_2$H$_5$ (isomer A) | —CHPh$_2$ / —H 59% | *—CH— / OC=O (phenyl) | powder | 3350, 1789, 1740, 1700sh. | 0.93t(7Hz)3H, 1.88dq(7;7Hz)2H, 3.40s3H, 3.4brs1H, 4.00s3H, 4.37s2H, 4.71s2H, (5.03s + 5.05 s)1H, 7.60s1H, 7.7-8.1m4H. |
| 7 | —C$_2$H$_5$ (isomer B) | —CHPh$_2$ / —H 75% | *—CH— / OC=O (phenyl) | powder | 3350, 1788, 1740, 1690sh. | 0.93t(7Hz)3H, 1.88dq(7;7Hz)2H, 3.37s3H, 3.4brs1H, 3.97s3H, (4.27s + 4.48s)2H, 4.70s2H, (5.00s + 5.03s)1H, 7.65s1H, 7.7-8.2m4H. |
| 8 | —C$_2$H$_5$ | —t-C$_4$H$_9$ / —H 86% | —CH$_2$OC=O / n-C$_9$H$_{19}$ | powder | 1790, 1750, 1710sh (CHCl$_3$). | 0.7-2.7m24H, 3.33t(7Hz)1H, 3.47s3H, 3.92s3H, 4.25s2H, 4.60 s2H, 5.03s1H, 5.90s2H (CDCl$_3$). |
| 9 | —C$_2$H$_5$ | —t-C$_4$H$_9$ | —CHPh$_2$ / —H 93% | powder | 3300, 1780, 1730sh, 1705, (CHCl$_3$). | 1.13t(7Hz)3H, 1.45s9H, 1.93dq (7;7Hz)2H, 3.17t(7Hz)1H, 3.53s 3H, 3.90s3H, 4.30s2H, 4.62s2H, 5.07s1H (CDCl$_3$). |
| 10 | —C$_2$H$_5$ | —Ph | —CHPh$_2$ / —H 78% | | 3320, 1785, 1765, 1705sh. | 1.00t(7Hz)3H, 2.00dq(7;7Hz)2H, 3.52s3H, 3.80t(7Hz)1H, (3.95s + 3.98s)3H, 4.27s2H, (4.60s + 4.65s)2H, 5.12s1H, 7.0-7.7m5H. |
| 11 | —C$_2$H$_5$ | —AOM | —CHPh$_2$ / —H quant | powder | | 0.98t(7Hz)3H, 1.93dq(7;7Hz)2H, 2.10s3H, 3.45t(7Hz)1H, 3.57s3H, 4.02s3H, 4.33s2H, 4.63s2H, 5.08 s1H, 5.78s2H (CDCl$_3$ + CD$_3$OD). |
| 12 | —C$_2$H$_5$ | —POM | —CHPh$_2$ / —H 48% | powder | | 0.95t(7Hz)3H, 1.16s9H, 1.89dq (7;7Hz)2H, 3.5brs1H, 3.45s3H, 3.94s3H, 4.28s2H, 4.61s2H, 5.04 s1H, 5.71s2H. |
| 13 | —i-C$_3$H$_7$ | —CHPh$_2$ / —H 88% | —CHPh$_2$ / —H | powder | 3300, 1784, 1723. | 1.00d(8Hz)3H, 1.02d(8Hz)3H, 2.4 m1H, (3.20d(8Hz) + 3.25(8Hz))1H, 3.47s3H, 4.00s3H, 4.35s2H, 4.67 s2H, 5.10s1H. |
| 14 | —i-C$_4$H$_9$ | —CHPh$_2$ / —H 88% | —CHPh$_2$ / —H | powder | 3300br, 1785, 1721. | 0.6–2.2m9H, 3.50t(7Hz)1H, 3.50 s3H, 4.00s3H, 4.40s2H, 4.65s 2H, 5.10s1H. |
| 15 | —n-C$_6$H$_{13}$ | —CHPh$_2$ / —H 92% | —CHPh$_2$ / —H 94% | powder | 3250br, 1785, 1720. | 0.7–2.2m13H, 3.47s3H, 3.5brs1H, 3.97s3H, 4.35s2H, 4.68s2H, 5.11s1H. |
| 16 | —CH$_2$CH=CH$_2$ | —CHPh$_2$ / —H 84% | —CHPh$_2$ / —H | powder | 3305br, 1785, 1720. | 2.63t(7Hz)2H, 3.48s3H, 3.55t (8Hz)1H, 4.00s3H, 4.33s2H, 4.65s2H, 4.8–5.3m2H, 5.08s1H, 5.6–6.3m1H. |
| 17 | —CH$_2$C≡CH | —CHPh$_2$ / —H quant | —CHPh$_2$ / —H | powder | 3280, 1785, 1722, 1685sh. | 2.05s1H, [2.70d(7Hz) + 2.74d(7Hz)] 2H, 3.50s3H, 3.75t(7Hz)1H, 3.98s3H, 4.30s2H, 4.61s2H, 5.07s1H. |

TABLE 3-continued

Deesterification in Tetrazolyl series (Het = Tetr)

| No. | R | B¹ | B² | shape | carboxylic acid product (6) IR: $\nu_{max}^{KBr}$ cm$^{-1}$ | NMR: $\delta_{ppm}^{CD3COCD3}$ (Hz value = J value) |
|---|---|---|---|---|---|---|
| 18 | —CH$_2$CH$_2$<br>\|<br>SCH$_3$ | —CHPh$_2$<br>—H 68% | —CHPh$_2$<br>—H | powder | 3300, 1780,<br>1720, 1685sh. | 2.05s3H, 2.2–2.7m4H, 3.50s3H,<br>3.7brs1H, 3.98s3H, 4.33s2H,<br>4.65s2H, (5.05s + 5.08s)1H. |
| 19 | —n-C$_3$H$_7$ | —CHPh$_2$<br>—H 88% | —CHPh$_2$<br>—H | powder | 3285br, 1785,<br>1721. | 0.7–2.1m7H, 3.49s3H, 3.5brs1H,<br>3.98s3H, 4.32s2H, 4.63s2H,<br>5.05s1H. |

EXAMPLE 2B

Deesterification in Thiadiazolyl series (Het=Tdz)

with AlCl$_3$

To a solution of diester (5) (1 weight) in a mixture of dichloromethane (5 to 10 weights) and anisole (3 to 10 weights) is added aluminum chloride (1 to 3 weights) at −20° C. The mixture is stirred at the same temperature for 1 hour. The reaction mixture is diluted with n-hexane to separate precipitate. This is collected by filtration. The filtrate is extracted with aqueous 5% sodium hydrogen carbonate. The extract is combined with above precipitate and washed with ether. The mixture is acidified with 2 N-hydrochloric acid, saturated with sodium chloride and extracted with methyl ethyl ketone. The extract is dried over magnesium sulfate and concentrated to dryness giving carboxylic acid (7).

with CF$_3$COOH

To a solution of the starting diester (5) (1 weight) in a mixture of dichloromethane (2 to 4 weights) and anisole (2 to 3 weights) is added trifluoroacetic acid (2 to 4 weights) and stirred for 1 to 3 hours. After concentration in vacuo, the reaction product is washed with petroleum ether to give objective carboxylic acid (7).

Compounds of Table 4 are prepared by these methods.

EXAMPLE 2C

Deesterification in Methylthiadiazolyl series (Het=MeTdz)

To a solution of ester (1 weight) in a mixture of dichloromethane (10 weights) and anisole (5 to 10 weights) cooled at −20° C. to 0° C. is added aluminum chloride (1 to 1.5 weights). After keeping at the same temperature for 1 to 2 hours, the reaction mixture is shaken with a mixture of ethyl acetate and diluted hydrochloric acid. Separated organic layer is washed with water, evaporated to remove the solvent and triturated with hexane to give the objective product as powder.

R=—C$_2$H$_5$, B¹=—CHPh$_2$→H, B²=—CHPh$_2$→H: Yield=29%.

IR: $\nu_{max}^{KBr}$ 1780, 1710, 1630 cm$^{-1}$.

NMR: $\delta_{ppm}^{CD3COCD3}$ 0.95t(7 Hz)3H, 2.03dq(7;7 Hz)2H, 2.73s3H, 3.48t(7 Hz)1H, 3.52s3H, (4.33d+4.52d)ABq(14 Hz)2H, 4.67s2H, 5.13s1H, 8.5brs1H.

EXAMPLE 3A

Esterification in Tetrazolyl series (Het=Tetr)

To an ice cold solution of carboxylic acid (6) (1 equivalent, 1 weight) in acetone (2 to 4 weights) is added 1.8 M/L-sodium 2-ethylhexanoate (1 to 2 equivalents), and the mixture is stirred for 30 minutes. The reaction mixture is diluted with ether, and separated salt is collected by filtration.

TABLE 4

Deesterification in Thiadiazolyl series (Het = Tdz)

| No. | R | B¹ | B² | shape | carboxylic acid product (7) IR: $\nu_{max}^{KBr}$ cm$^{-1}$ | NMR: $\delta_{ppm}^{CD3COCD3}$ (Hz value = J value) |
|---|---|---|---|---|---|---|
| 1 | —CH$_3$ | —CHPh$_2$<br>—H 88% | —CHPh$_2$<br>—H | powder | ca3300, 1782,<br>1740. | (1.33d(7Hz) + 1.37d(7Hz))3H,<br>3.48s3H, 3.6brs1H, (4.45s + 4.50<br>s)2H, 4.63s2H, 5.08s1H, 9.42s1H. |
| 2 | —C$_2$H$_5$ | —CHPh$_2$<br>—H 90% | —CHPh$_2$<br>—H | powder | ca3300, 1784,<br>1720. | 0.93t(7Hz)3H, 1.90dq(7;7Hz)2H,<br>3.5brs1H, 3.48s3H, (4.44s + 4.49<br>s)2H, 4.63s2H, 5.08s1H, 9.40s1H |
| 3 | —C$_2$H$_5$ | —POM | —CHPh$_2$<br>quant<br>—H | powder | | 0.96t(7Hz)2H, 1.21s9H, 1.90dq<br>(7;7Hz)2H, 3.50t(7Hz)1H, 3.52s<br>3H, (4.40d + 4.60d) ABq(14Hz)2H,<br>4.68s2H, 5.12s1H, 5.80s2H, 8.21<br>d(8Hz)1H, 9.40s1H. |
| 4 | —n-C$_3$H$_7$ | —CHPh$_2$<br>—H 88% | —CHPh$_2$<br>—H | powder | ca3300, 1785,<br>1740. | 0.7–2.1m7H, 3.48s3H, 3.5brs1H,<br>(4.45s + 4.50s)2H, 4.63s2H,<br>5.08s1H, 9.40s1H. |
| 5 | —n-C$_4$H$_9$ | —CHPh$_2$<br>—H 95% | —CHPh$_2$<br>—H | powder | | 0.7–2.2m9H, 3.48s3H, 3.5brs1H,<br>(4.43s + 4.48s)2H, 4.65s2H,<br>5.12s1H, 9.40s1H. |
| 6 | —CH$_2$CH=CH$_2$ | —CHPh$_2$<br>—H 57% | —CHPh$_2$<br>—H | powder | 3250, 1782,<br>1720. | 2.62t(7Hz)2H, 3.47s3H, 3.47t<br>(7Hz)1H, (4.33s + 4.48s)2H,<br>4.63s2H, 4.8–5.3m2H, 5.09s1H,<br>5.5–6.3m1H, 9.42s1H. |

When the esterifying reagent is chloride or bromide, the salt is dissolved in acetone (4 to 10 weights), mixed with the esterifying reagent (1 to 2 equivalents) and sodium iodide (1 to 2 equivalents) in acetone (2 to 3 weights) and stirred for 1 to 2 hours. When the esterifying reagent is bromide or iodide, the salt is dissolved in N,N-dimethylformamide or N,N-dimethylacetamide (4 to 5 weights), mixed with the esterifying reagent (1 to 2 equivalents) in the same solvent (1 to 3 weights) and stirred for 0.5 to 2 hours.

The mixture is diluted with ethyl acetate, washed with water, dried over sodium sulfate and concentrated in vacuo. The residue is purified by chromatography over silica gel containing 10% water to afford desired ester (8).

By using one of these methods, the compounds of Table 5 are prepared.

TABLE 5

Esterification in Tetrazolyl series (Het = Tetr)

| No. | R | $B^1$ | $B^2$ | ester product (8) shape | IR: $\nu_{max}^{CHCl_3}$cm$^{-1}$ | NMR: $\delta_{ppm}^{CDCl_3}$(Hz value = J value) |
|---|---|---|---|---|---|---|
| 1 | —CH$_3$ | —H, —Na, —AOM  87% 70% | —CHPh$_2$ | powder | | 1.47d(8Hz)3H, 2.07s3H, 3.48 q(8Hz)1H, 3.55s3H, 3.78s3H, 4.25s2H, 4.62s2H, 5.03s1H, 5.75s2H, 6.88s1H, 7.08–7.67m. |
| 2 | —CH$_3$ | —Na, —AOM  35% | —Na, —AOM | powder | 3415, 3360, 1790, 1770, 1745, 1711, 1632. | 1.47d(8Hz)3H, 2.10s3H, 2.15s 3H, 3.45q(8Hz)1H, 3.52s3H, 3.92s3H, 4.27brs2H, 4.62s2H, 5.03s1H, 5.77s2H, (5.83d + 5.98d)ABq(6Hz)2H. |
| 3 | —CH$_3$ | —AOM | —CHPh$_2$, —H, —Na, —POM  99% 23% | powder | 3415, 3360, 1792, 1756, 1715, 1633. | 1.23s9H, 1.47d(8Hz)3H, 2.10s 3H, 3.47q(8Hz)1H, 3.52s3H, 3.90s3H, 4.28s2H, 4.63s2H, 5.03s1H, 5.77s2H, (5.85d + 6.02d)ABq(6Hz)1H. |
| 4 | —CH$_3$ | —H, —Na, —POM  87% 82% | —CHPh$_2$ | powder | | 1.18s9H, 1.47d(8Hz)3H, 3.45q (8Hz)1H, 3.55s3H, 3.78s3H, 4.27s2H, 4.62s2H, 5.05s1H, 5.78s2H, 6.88s1H, 7.15–7.68m |
| 5 | —CH$_3$ | —POM | —CHPh$_2$, —H, —Na, —AOM  94% 29% | powder | 3420, 3345, 1791, 1756, 1712, 1633. | 1.20s9H, 1.47d(8Hz)3H, 2.15s 3H, 3.43q(8Hz)1H, 3.52s3H, 3.90s3H, 4.27brs2H, 4.60s2H, 5.03s1H, 5.77s2H, (5.83d + 5.98d)ABq(6Hz)1H. |
| 6 | —CH$_3$ | —H, —Na, —POM  72% 47% | —H, —Na, —POM | powder | 3400, 1791, 1752, 1710sh, 1632. | 1.20s9H, 1.23s9H, 1.47d(7Hz) 3H, 3.43q(7Hz)1H, 3.52s3H, 3.90s3H, 4.27s2H, 4.62s2H, 5.03s1H, 5.77s2H, (5.85d + 6.00d)ABq(6Hz)2H. |
| 7 | —C$_2$H$_5$ | —H, —Ph  80% | —CHPh$_2$ | powder | 3300, 1785, 1710. | 1.03t(7Hz)3H, 2.08dq(7;7Hz)2H, 3.50s3H, 3.5brs1H, 3.66s3H, 4.15 s2H, 4.53s2H, 5.03s1H, 6.83s1H. |
| 8 | —C$_2$H$_5$ | —t-C$_4$H$_9$ | —H, —CH$_2$OC=O, n-C$_9$H$_{19}$  33% | | 3400, 1792, 1745, 1712. | 0.6–2.7m24H, 1.45s9H, 3.15t(7Hz) 1H, 3.53s3H, 3.92s3H, 4.30s2H, 4.63s2H, 5.05s1H, 5.83d(5Hz)1H, 5.98d(5Hz)1H. |
| 9 | —C$_2$H$_5$ (isomer A) | —t-CH$_4$H$_9$ | —H, —CH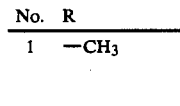  33% | powder | 3300, 1790, 1738, 1710. | 0.90t(7Hz)3H, 1.43s9H, 1.87dq (7;7Hz)2H, 3.10t(7Hz)1H, 3.43s 3H, 3.92s3H, 4.30s2H, 4.70s2H, 5.02s1H, 7.40s1H, 7.5–8.0m4H. |
| 10 | —C$_2$H$_5$ (isomer B) | —t-C$_4$H$_9$ | —H, —CH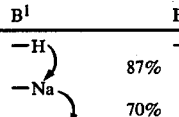  33% | powder | 3300, 1790, 1736, 1710. | 0.90t(7Hz)3H, 1.44s9H, 1.87dq(7; 7Hz)2H, 3.11t(7Hz)1H, 3.45s3H, 3.91s3H, (4.17s + 4.40s)2H, 4.63s 1H, 5.05s1H, 7.47s1H, 7.5–8.0m4H |
| 11 | —C$_2$H$_5$ | —H, —Na, —POM  81% 82% | —CHPh$_2$ | powder | | 0.97t(7Hz)3H, 1.23s9H, 1.97dq (7;7Hz)2H, 3.28t(7Hz)1H, (3.52 s + 3.55s)3H, 3.58s3H, 4.23s2H, 4.58s2H, 5.02s1H, (5.68d + 5.81d) ABq(6Hz)2H, 6.87s1H. |
| 12 | —C$_2$H$_5$ | —POM | —H, —Na, —AOM  quant 70% | powder | 3350, 1790, 1755, 1705. | 0.97t(7Hz)3H, 1.20s9H, 1.98dq (7;7Hz)2H, 2.15s3H, 3.28t(7Hz) 1H, (3.50s + 3.52s)3H, 3.90s3H, (4.21d + 4.38d)ABq(12Hz)2H, 4.60 s2H, 5.03s1H, (5.73d + 5.83d)ABq (6Hz)2H, 7.48d(4Hz)1H. |
| 13 | —C$_2$H$_5$ | —H, | —H | powder | 3350, 1792, | 0.98t(7Hz)3H, 1.30s9H, 1.40s9H, |

TABLE 5-continued

Esterification in Tetrazolyl series (Het = Tetr)

| No. | R | B¹ | B² | | shape | IR: $\nu_{max}^{CHCl_3}$cm$^{-1}$ | ester product (8) NMR: $\delta_{ppm}^{CDCl_3}$(Hz value = J value) |
|---|---|---|---|---|---|---|---|
|  |  | —Na<br>—POM | quant<br>44% | —Na<br>—POM |  | 1755, 1702. | 1.98dq(7;7Hz)2H, 3.28t(7Hz)1H, (3.50s + 3.52s)3H, 3.91s3H, 4.27 s2H, 4.60s2H, 5.03s1H, (5.73d + 5.83d)ABq(6Hz)2H, (5.84d + 6.00d) ABq(6Hz)1H, 7.47d(4Hz)1H. |
| 14 | —C₂H₅ | —H<br>—Na<br>—AOM | 81%<br>51% | —CHPh₂ | powder |  | 0.96t(7Hz)3H, 1.98dq(7;7Hz)2H, 2.03s3H, 3.35t(7Hz)1H, 3.53s + 3.55s)3H, 3.73s3H, 4.23s2H, 4.61s2H, 5.05s1H, 5.73s2H, 6.90s1H. |
| 15 | —C₂H₅ | —H<br>—Na<br>—AOM | quant<br>11% | —H<br>—Na<br>—AOM | powder | 3350, 1790, 1770, 1740, 1700sh. | 0.96t(7Hz)3H, 1.95dq(7;7Hz)2H, 2.08s3H, 2.15s3H, 3.32t(7Hz)1H, 3.53s3H, 3.96s3H, (4.23d + 4.40d) ABq(14Hz)2H, 4.63s2H, 5.05s1H, 5.75s2H, (5.85d + 5.97d)ABq(5Hz)2H |
| 16 | —C₂H₅ | —AOM | —H<br>—Na<br>—POM | 96%<br>32% | powder | 3350, 1792, 1755, 1710. | 0.98t(7Hz)3H, 1.24s9H, 2.00dq (7;7Hz)2H, 2.12s2H, 3.28t(7Hz) 1H, (3.50s + 3.51s)3H, 3.88s3H, 4.25s2H, 4.58s2H, 5.00s1H, 5.73s2H, (5.83 + 5.97d)ABq(5Hz) 2H, 7.3brs1H. |

Esterification through acid chloride to give the compound No. 7 in Table 5

By the action of pyridine (1.5 equivalents) and oxalyl chloride (1.2 equivalents) to a solution of 7β-(2-ethyl-2-carboxyacetamido)-7α-methoxy-3-(1-methyl-5-tetrazolyl)-thiomethyl-1-oxa-1-dethia-3-cephem-4-carboxylic acid diphenylmethyl ester (1 equivalent) in dichloromethane (11 weights) at 0° C. for 1 hour, acid chloride is prepared. To this solution is added phenol (2 equivalents) and pyridine (1.5 equivalents), and stirring continued for 30 minutes. The reaction mixture is diluted with ethyl acetate, washed with 2 N-hydrochloric acid and water, dried over magnesium sulfate and concentrated. The residue is chromatographed over silica gel containing 10% water (34 weights). The fraction eluted with a mixture of benzene and ethyl acetate (10:1) affords 7β-(2-ethyl-2-phenoxycarbonylacetamido)-7α-methoxy-3-(1-methyl-5-tetrazolyl)thiomethyl-1-oxa-1-dethia-3-cephem-4-carboxylic acid diphenylmethyl ester (0.8 equivalents).

EXAMPLE 3B

Esterification in Thiadiazolyl series (Het=Tdz)

To an ice cooled solution of a sodium salt (1 equivalent, 1 weight) in N,N-dimethylformamide or N,N-dimethylacetatamide (4 to 8 weight) is added pivaloyloxymethyl iodide (2 to 4 equivalents). The mixture is stirred for 1 to 2 hours. About 30 minutes after addition of a small amount of thiourea for decomposing the remaining iodide reagent, the reaction mixture is poured onto water and extracted with ethyl acetate. The extract is washed with water, dried over magnesium sulfate, and concentrated under reduced pressure. The residue is purified by chromatography over silica gel. The fraction eluted with a mixture of benzene and ethyl acetate (2:1) affords powder of ester (9) after lyophilization.

A method similar to that of Example 3A can also be applied.

Thus, compounds of Table 6 are prepared by the methods given above.

TABLE 6

Esterification in Thiadiazolyl series (Het = Tdz)

| No. | R | B¹ | B² | | shape | IR: $\nu_{max}^{CHCl_3}$cm$^{-1}$ | ester product (9) NMR: $\delta_{ppm}^{CDCl_3}$(Hz value = J value) |
|---|---|---|---|---|---|---|---|
| 1 | —CH₃ | —Na<br>—POM | 47% | —Na<br>—POM | powder | 3415, 1791,<br>1753, 1711. | 1.20s9H, 1.23s9H, 1.45d(7Hz)3H, 3.50q(8Hz)1H, 3.53s3H, (4.25d + 4.63d)ABq(14Hz)2H, 4.65s2H, 5.08s1H, 5.80s2H, (5.93d + 6.05d) ABq(6Hz)2H, 9.08s1H. |
| 2 | —C₂H₅ | —H<br>—Na<br>—POM | quant<br>46% | —CHPh₂ | powder | 3350, 1788,<br>1750, 1720. | 0.98t(7Hz)3H, 1.19s9H, 2.00dq (7;7Hz)2H, 3.31t(7Hz)1H, (3.52s + 3.55s)3H, (4.27d + 4.50d)ABq(14 Hz)1H, 4.59s2H, 5.04s1H, (5.73d + 5.83d)ABq(5Hz)2H, 7.60s1H, 8.98s1H. |
| 3 | —C₂H₅ | —POM | —H<br>—Na<br>—AOM | 32% | powder | 3350, 1790,<br>1755, 1705. | 0.97t(7Hz)3H, 1.19s9H, 1.98dq (7;7Hz)2H, 2.14s3H, 3.28t(7Hz) 1H, (3.49s + 3.51s)3H, (4.23d + 4.60d)ABq(14Hz)2H, 4.60s2H, 5.02s1H, (5.73d + 5.83d)ABq(6Hz) 2H, (5.87d + 5.98d)ABq(6Hz)2H, 7.5brs1H, 9.07s1H. |
| 4 | —C₂H₅ | —H<br>—Na<br>—POM | quant<br>22% | —H<br>—Na<br>—POM | powder | 3350, 1790,<br>1755, 1705. | 0.97t(7Hz)3H, 1.19s9H, 1.23s9H 1.98dq(7;7Hz)2H, 3.27t(7Hz)1H, (3.48s + 3.51s)3H, (4.23d + 4.57d) ABq(14Hz)2H, 4.57s2H, 5.03s1H, (5.73d + 5.83d)ABq(5Hz)2H, (5.87d |

TABLE 6-continued

| | | | | | Esterification in Thiadiazolyl series (Het = Tdz) | |
|---|---|---|---|---|---|---|
| | | | | | ester product (9) | |
| No. | R | B¹ | B² | shape | IR: $\nu_{max}^{CHCl_3}$cm$^{-1}$ | NMR: $\delta_{ppm}^{CDCl_3}$(Hz value = J value) |
| | | | | | | + 6.02d)ABq(6Hz)2H, 7.47d(4Hz) 1H, 9.07s1H. |

EXAMPLE 3C

Esterification in Methylthiadiazolyl series
(Het=MeTdz)

To a solution of sodium salt (1 weight, 1 equivalent) in dimethylformamide (5 to 6 weights) is added pivaloyloxymethyl iodide (4 to B 5 equivalents) and stirred at the same temperature for 30 minutes to 1 hour. The reaction mixture is shaken with a mixture of ethyl acetate and ice water. The organic layer is washed with water, dried over magnesium sulfate, and evaporated to remove the solvent. The residue is chromatographed over silica gel containing 10% water to give the fraction eluted with a mixture of benzene and ethyl acetate (7:1) which is then lyophilized to afford objective product.

R=C₂H₅, B¹=Na→POM, B²=—Na→—POM, Yield: 60%.

IR: $\nu_{max}^{CHCl_3}$ 3350, 1780, 1740, 1700sh cm$^{-1}$.

NMR: $\delta_{ppm}^{CDCl_3}$ 0.97t(7 Hz)3H, 1.20s9H, 1.25s9H, 1.98dq(7;7 Hz)2H, 2.72s3H, 3.27t(7 Hz)1H, 3.53s3H, (4.20d+4.53d)ABq(14 Hz)2H, 4.58s2H, 5.03s1H, (5.73d+5.83d)ABq(5 Hz)2H, (5.86d+6.00d) ABq(5 Hz)2H, 7.4brs1H.

EXAMPLE 4

Salt formation

Lyophilization

A suspension of dicarboxylic acid (6) or (7) (1 equivalent) in (10 weights) of water is mixed with powdered sodium hydrogen carbonate (2 equivalents) under ice cooling to give transparent solution (pH≈7.5), which is then purified with High-porous polymer HP-20 (product of Mitsubishi Kasei Kogyo K. K.) and lyophilized to give disodium salt (10) (0.8 weights).

Precipitation

To a cold solution of the free acid in methanol (2 to 3 weights) is added a solution of 1.8 M-sodium 2-ethylhexanoate in methanol (1 to 1.2 equivalents). After 10 to 30 minutes, the reaction mixture is diluted with a mixture of ether and ethyl acetate (2:1) to precipitate the desired sodium salt, which is collected by filtration.

By one of above methods the compounds of Table 7 are prepared.

Minimal inhibitory concentration

The disodium salts (10) showed the following minimal inhibitory concentration in the Table 8, when assayed their antibacterial activity in vitro against *Escherichia coli* EC-14 by serial dilution method on Mueller Hinton agar nutrient medium.

TABLE 7

| | | | | | | | salt product (10) | |
|---|---|---|---|---|---|---|---|---|
| No. | R | B¹ | | B² | | Het | shape | IR: $\nu_{max}^{Nujol}$cm$^{-1}$ | NMR: $\delta_{ppm}^{CDCl_3}$(Hz value = J value) |
| 1 | —CH₃ | —CHPh₂, —H, —Na | 72% | —CHPh₂, —H, —Na | | Tetr | powder | 3360, 3240, 2640, 1765, 1675, 1602. | (1.35d(8Hz) + 1.37d(8Hz))3H, 3.25q(8Hz)1H, 3.45s3H, 3.95 s3H, 4.33s2H, 4.53s2H, 5.02s1H (CD₃OD). |
| 2 | —CH₃ | —AOM | | —H, —Na | 99% | Tetr | powder | 3250br, 1775, 1765, 1690, 1680, 1640, 1605. | 1.38m3H, 2.07s3H, 3.52s2H, 4.00s3H, 4.50m2H, 4.65brs2H, 5.08s1H, 5.78s2H(CD₃COCD₃). |
| 3 | —CH₃ | —POM | | —H, —Na | 94% | Tetr | powder | 3250br, 1760, 1685, 1605. | 1.17s9H, 1.35br3H, 3.48s3H, 3.93s3H, 4.50m4H, 5.02s1H, 5.75s2H(CD₃COCD₃). |
| 4 | —C₂H₅ | —H, —Na | 81% | —H, —Na | | Tetr | powder | 3400br, 1770, 1680, 1605 (KBr). | 0.93t(7Hz)3H, 1.89dq(7;7Hz) 2H, 3.07t(7Hz)1H, 3.50s3H, 4.00s2H, 4.39s2H, 4.57s2H, 5.07s1H(CD₃OD). |

| | | | | | | | salt product (10) | |
|---|---|---|---|---|---|---|---|---|
| No. | R | B¹ | | B² | | Het | shape | IR: $\nu_{max}^{KBr}$cm$^{-1}$ | NMR: $\delta_{ppm}^{CD_3OD}$(Hz value ≠ J value) |
| 5 | —CH₃ | —CHPh₂, —H, —Na | 51% | —CHPh₂, —H, —Na | | Tdz | powder | 3400, 1768, 1670, 1605. | 1.34d(7Hz)3H, 3.18q(7Hz)1H, 3.43s3H, (4.30d + 4.52d)ABq (14Hz)2H, 4.50s2H, 4.98s1H, 9.36s1H. |
| 6 | —C₂H₅ | —H, —Na | quant | —H, —Na | | Tdz | powder | 3400, 1765, 1670, 1605. | 0.94t(7Hz)3H, 1.87dq(7;7Hz) 2H, 3.01t(7Hz)1H, 3.42s3H, (4.33d + 4.57d)ABq(14Hz)2H, 4.50s2H, 4.98s1H, 9.37s1H. |
| 7 | —C₃H₇ | —H, —Na | quant | —H, —Na | | Tdz | powder | 3400, 1768, 1670, 1605. | 0.90t(7Hz)3H, 1.2-2.00m4H, 3.26t(7Hz)1H, 3.43s3H, (4.33 d + 4.56d)ABq(14Hz)2H, 4.50s 2H, 4.98s1H, 9.36s1H. |

TABLE 8

| MIC of Sodium salts | | | | |
|---|---|---|---|---|
| Het=Tetr | | | Het=Tdz | |
| No. | R | MIC (μg/ml) | No. | R | MIC (μg/ml) |
| 1 | —H | 1.56 | 1 | —CH₃ | 0.39 |
| 2 | —CH₃ | 0.2 | 2 | —C₂H₅ | 0.2 |

TABLE 8-continued

| | MIC of Sodium salts | | | |
|---|---|---|---|---|
| Het=Tetr | | | Het=Tdz | |
| No. | R | MIC (μg/ml) | No. R | MIC (μq/ml) |
| 3 | —$C_2H_5$ | 0.1 | 3  -n-$C_3H_7$ | 0.2 |
| 4 | -n-$C_3H_7$ | 0.1 | 4  -n-$C_4H_9$ | 0.39 |
| 5 | -i-$C_3H_7$ | 0.39 | 5  —$CH_2CH$=$CH_2$ | 0.39 |
| 6 | -i-$C_4H_9$ | 0.39 | | |
| 7 | -n-$C_6H_{13}$ | 12.5 | | |
| 8 | —$CH_2CH$=$CH_2$ | 0.2 | | |

EXPERIMENT

Five representative compounds in the preceding examples are assayed for protection of mice from infection caused by *Pseudomonas aeruginosa* to give the effects as in the following table.

TABLE 9

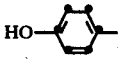

$ED_{50}$ ( two subc. inj. (given mg/kg each) 1 and 5 hrs after intraperitoneal inoculation )

| | | | P. aeruginosa | |
|---|---|---|---|---|
| Comp. No. | $R^1$ | Het* | CN-5* | PS-24** |
| 1 | $CH_3$— | Tetr | 22.3 | 11.1 |
| 2 | $C_2H_5$— | " | 22.2 | 17.7 |
| 3 | $CH_3$— | Tdz | 33.8 | 12.6 |
| 4 | $C_2H_5$— | " | 32.5 | 15.5 |
| 5 | n-$C_3H_9$— | " | 39.3 | 10.4 |
| Reference | 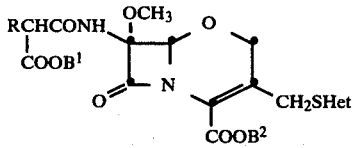 HO— | Tetr | 44.5 | 20.4 |

*inoculation = 7 × $10^3$
**inoculation = 1 × $10^4$

What we claim is:
1. A compound of the following formula

RCHCONH—OCH₃ ... (structure)

wherein

R is $C_1$ to $C_6$-alkyl, $C_2$ to $C_5$-alkenyl, $C_2$ to $C_5$-alkynyl or $C_1$ to $C_2$-alkylthio-$C_1$ to $C_2$-alkyl;

Het is a member selected from the group consisting of 2-methyl-1,3,4-thiadiazol-5-yl, 1-methyl-5-tetrazolyl, and 2-thiadiazolyl; and $B^1$ and $B^2$ each is (1) a hydrogen atom, (2) an ester protecting group selected from the group consisting of mono- or di-cyclic aralkyl, $C_4$ to $C_{10}$-tertiary alkyl, $C_1$ to $C_{10}$-β-haloalkyl and $C_3$ to $C_8$-β-alkylsulfonylalkyl, (3) a pharmaceutically acceptable ester selected from the group consisting of straight or branched chain $C_3$ to $C_{19}$-alkanoyloxyalkyl, $C_3$ to $C_6$-alkoxycarbonyloxyalkyl, $C_4$ to $C_6$-tertiary alkyl, $C_7$ to $C_{13}$-aralkyl and $C_7$ to $C_9$-aryl, and (4) a pharmaceutically acceptable salt forming atom or group.

2. A compound according to claim 1 wherein R is $C_1$ to $C_3$-alkyl.

3. A compound according to claim 2 wherein R is methyl or ethyl.

4. A compound according to claim 1 wherein $B^1$ or $B^2$ is a light metal atom.

5. A compound according to claim 4 wherein $B^1$ or $B^2$ is sodium.

6. A compound according to claim 1 wherein the ester group is $C_2$ to $C_5$-alkanoyloxy-$C_1$ or $C_2$-alkyl, phenyl or phthalidyl.

7. A compound according to claim 6 wherein the ester forming group is acetoxymethyl or pivaloyloxymethyl.

8. A compound according to claim 1 wherein R is $C_1$ to $C_3$ alkyl and $B^1$ and $B^2$ each is hydrogen, a pharmaceutically acceptable salt or a pharmaceutically acceptable ester group as defined in claim 1.

9. A compound according to claim 8 wherein $B^1$ and $B^2$ each is hydrogen or sodium.

10. A compound according to claim 8 wherein $B^1$ or $B^2$ is $C_2$ to $C_5$-alkanoyloxy-$C_1$ to $C_2$-alkyl.

11. A compound according to claim 8 wherein $B^1$ and $B^2$ each is hydrogen or sodium.

12. A compound according to claim 8 wherein $B^1$ or $B^2$ is acetoxymethyl or pivaloyloxymethyl.

13. A compound according to claim 11 or claim 12 wherein R is methyl or ethyl.

14. An antibacterial composition comprising an antibacterially effective amount of a compound according to claim 1 as an active ingredient and a pharmaceutically acceptable carrier therefor.

15. A method for treating or preventing human or veterinary bacterial infection caused by sensitive bacteria by administering an antibacterially effective amount of a compound according to claim 1.

* * * * *